Figure 1:
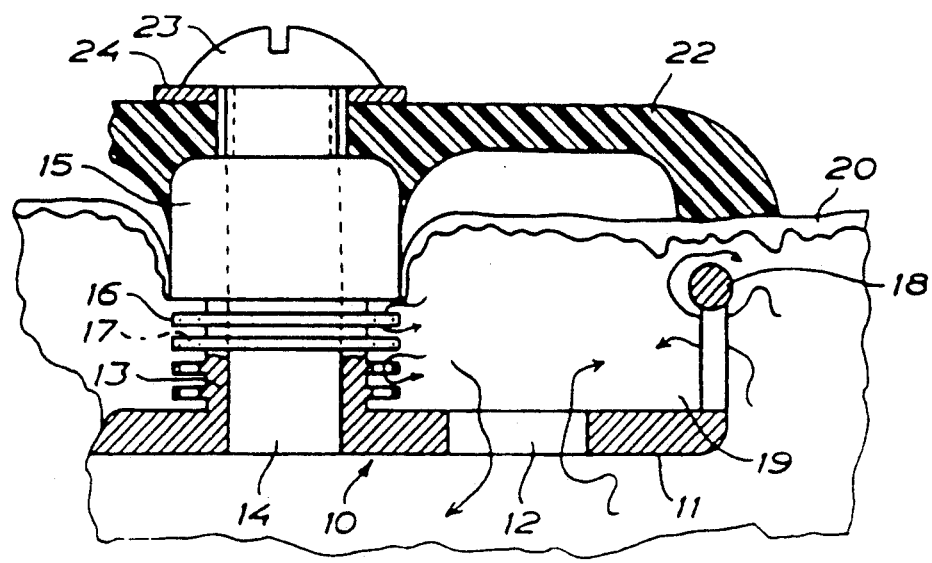

United States Patent [19]

Lundgren

[11] Patent Number: 5,098,398
[45] Date of Patent: Mar. 24, 1992

[54] IMPLANT PASSAGEWAY

[76] Inventor: Dan Lundgren, Kyrkvägen 5, Hovås, Sweden, S-430 80

[21] Appl. No.: 263,778
[22] PCT Filed: Apr. 21, 1987
[86] PCT No.: PCT/SE87/00201
§ 371 Date: Dec. 19, 1988
§ 102(e) Date: Dec. 19, 1988
[87] PCT Pub. No.: WO87/06122
PCT Pub. Date: Oct. 22, 1987

[30] Foreign Application Priority Data

Apr. 18, 1986 [SE] Sweden .............................. 8601815-7

[51] Int. Cl.⁵ ............................................. A61M 5/32
[52] U.S. Cl. ........................... 604/175; 128/DIG. 26; 623/12
[58] Field of Search ................. 604/175, 93, 891.1, 604/264, 8, 27, 29, 48; 128/898, 899, DIG. 26; 623/11, 12, 2; 606/15

[56] References Cited

U.S. PATENT DOCUMENTS

| | | | |
|---|---|---|---|
| 3,663,965 | 5/1972 | Lee, Jr. et al. | 604/175 |
| 3,752,162 | 8/1973 | Newash | 604/264 |
| 4,015,601 | 4/1977 | Bokros et al. | 604/175 |
| 4,217,664 | 8/1980 | Faso | 604/175 |
| 4,425,119 | 1/1984 | Berglund | 604/175 |
| 4,534,760 | 8/1985 | Raible | 604/175 |
| 4,534,761 | 8/1985 | Raible | 128/899 |
| 4,704,126 | 11/1987 | Baswell et al. | 623/12 |
| 4,781,176 | 11/1988 | Ravo | 623/12 |
| 4,781,694 | 11/1988 | Branemark et al. | 604/175 |

Primary Examiner—C. Fred Rosenbaum
Assistant Examiner—Kathleen A. Daley
Attorney, Agent, or Firm—Merchant & Gould, Smith, Edell, Welter & Schmidt

[57] ABSTRACT

Implant passageway for connection of body cavities or body vessels to a device, container or the like externally of the body. It comprises an element (11) which consists of a biocompatible material or has a biocompatible outside layer. This element forms a socket (13) with a through passage (14) and on the outside of the curved surface thereof inwardly of an end portion (15) having a smooth outside surface, forms radial flanges (16) mutually spaced axially and defining between radial surfaces thereof peripheral grooves for growth of surrounding tissue thereinto.

6 Claims, 2 Drawing Sheets

IMPLANT PASSAGEWAY

The invention relates to an implant passageway for connection of body cavities or body vessels to a device, container or the like externally of the body, comprising an element which consists of a biocompatible material or has a biocompatible outside layer and which includes a socket with a through passage.

Such an implant passageway can be used e.g. for establishing a permanent connection to the abdomen of persons who from time to time have to be subject to e.g. peritoneal dialysis, or for establishing a temporary connection to a body cavity. The difficulty when arranging an implant passageway is above all that the epithelium cells grow along the passageway, rejection from the body being the consequence thereof.

This difficulty is overcome by the implant passageway of the invention having obtained the characteristics of claim 1.

Figure 2:
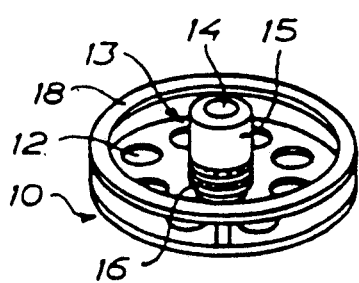
Figure 3:
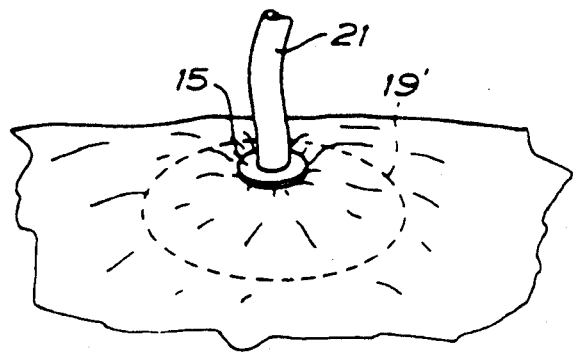
Figure 4:
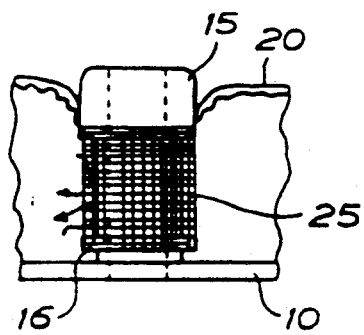
Figure 5:
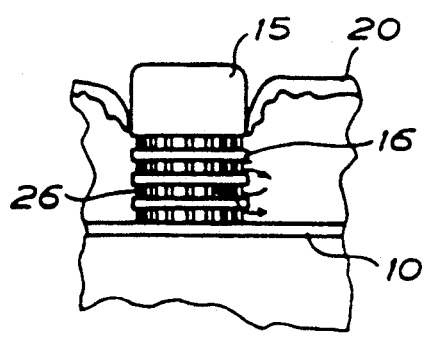
Figure 6:
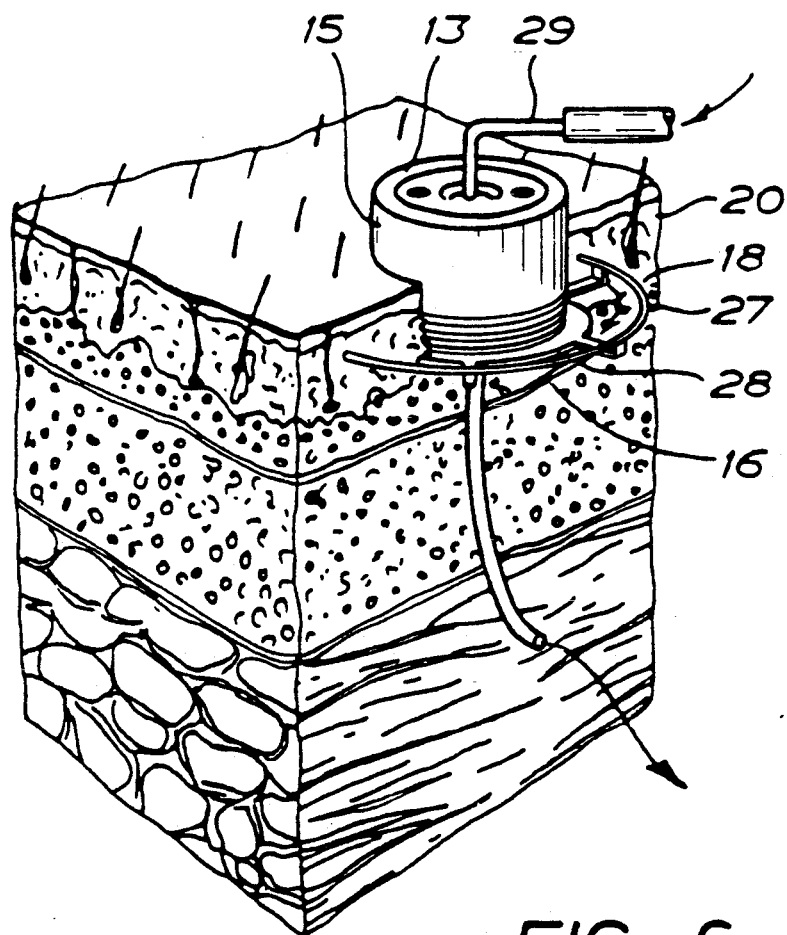

In order to explain the invention in more detail an embodiment thereof will be described below, reference being made to the accompanying drawing in which FIG. 1 is a fragmentary axial sectional view of an implant passageway of the invention in one embodiment thereof, FIG. 2 is a perspective view on a reduced scale of the element of the implant passageway of FIG. 1 which is to be positioned partly under the skin, FIG. 3 is a perspective view showing the implanted passageway, FIG. 4 is a fragmentary axial sectional view of another embodiment of the implant passageway, FIG. 5 is a fragmentary axial sectional view of a third embodiment of the implant passageway, and FIG. 6 is a perspective sectional view of the implant passageway of FIGS. 1 to 3 slightly modified.

In the embodiment of FIGS. 1, 2, and 3, the implant passageway comprises an element 10 which is to be implanted in the tissue under the skin. This element should be made of a biocompatible material or should at least be coated with such material on the surface thereof. The material can be a metal or a metal alloy. The preferred metal is titanium, but also aluminium, indium, zirkonium and molybdenum can be used in this connection, and suitable alloys can contain cobalt-nickel-chromium, cobalt-chromium-molybdenum, or aluminium-vanadium-titanium. Also biocompatible polymers can be used such as polyethylene, silicone, or polyurethane of the highest medical quality. When the element is coated with one of the metals or metal alloys mentioned above on the outside thereof, the coating can be made by evaporation in vacuum and can have a thickness of the order of 50 to 300 nm.

The element 10 comprises a circular base plate 11 having through apertures 12. On the base plate, a central socket 13 is provided which forms a through cylindrical passage. The socket projects from the upper side of the plate 11 and the outer end of the socket can be shaped for connection e.g. to a hose, or for connection to a container, a plastic bag, a syringe, or any other device. Adjacent the outer end the socket has a portion 15 having a smooth curved surface. Said portion tapers slightly towards the outer end and has curved end edges, a number of flanges 16 with apertures 17 being arranged inwardly of portion 15. The flanges are spaced radially from each other and define peripheral grooves between radial surfaces. At the outer edge the base plate 10 has a circumferential apertured fence 18 which is thus spaced from the socket 13 so that there is provided on the upper side of the base plate an annular free zone 19 between the socket and the fence. The fence as shown here forms a ring supported by uprights, and this ring can have round cross-sectional shape as in FIG. 1 or square cross-sectional shape as in FIG. 2.

When the element 10 is implanted on a human being or on an animal, portion 15 of the socket 13 extends through the epithelium layer 20, the flanges 16, the base plate 11, and the fence 18 being located under the epithelium layer. Then, the connective tissue around the element can grow into the space between the flanges 16 and through the apertures 17 therein, and it can also grow through the apertures 12 in the base plate 11 and around the fence 18 as has been indicated by arrows in FIG. 1. The epithelium 20 grows downwards along the smooth end portion 15 but will then be stopped by the growth of connective tissue taking place below this portion. Thus, in the region between the socket and the fence connective tissue will be present, region 19 forming an (immobilized) zone relieved from external stretching of the skin by the fence boundary. Said zone is indicated by a dot-and-dash line 19' in FIG. 3. By this arrangement the element 10 will be firmly fixed in the connective tissue, avoiding mechanically induced irritation-inflammation around the socket 13 which projects from the tissue through the epithelium. In FIG. 3, it is illustrated how a catheter 21 is connected to the implant passageway.

In order to fix the element during healing a round or star-shaped plastic disk 22 e.g. of polytetrafluoro ethylene or another hydrofobic plastic material can be secured to the socket 13 by means of a screw 23 and an intermediary washer 24, the passage 14 being internally threaded of course. The disk 22 engages the outside of the skin in the region of the fence 18 and can be pressed more or less heavily against the epithelium layer 20 by tightening the screw 23. This disk can be left on the socket also after completion of the healing.

In order to achieve a satisfactory growth of connective tissue into the flanges 16 it has been found suitable to have a spacing of the flanges which is at least 0.08 mm and to have a depth of the groove between adjacent flanges which is at least 0.08 mm.

The flanges can form a beaded edge supplementing the apertures 17 or replacing such apertures so that there is provided between adjacent flanges an undercut groove which the tissue can grow into.

In the embodiment of FIG. 4, the socket is surrounded by a net envelope 25 spaced from the curved surface of the socket. Connective tissue can grow through this net envelope to anchor the element 10, the flanges on the socket being provided as spacers for the net envelope.

In the embodiment of FIG. 5, the flanges 16 form apertures therein and axially extending rods 26 are passed through these apertures so that the connective tissue can grow into the grooves between the flanges around the rods 26 extending across the grooves.

The socket 13 and the fence 18 can project from one and the same side of the base plate 11 as shown in the drawing but they can also project from both sides of the base plate.

In the embodiment of FIG. 6, the fence 18 is supported by radial arms 27 projecting from a peripheral flange 28 on the socket 13. A hose connection 29 is passed through the socket.

I claim:

1. Implant passageway for connection of a body cavity with a device external to the body, comprising a base plate, a socket attached thereto and having a through passage, at least the surfaces of said socket being of a biocompatible material, said socket having an end portion projecting from the base plate and having a smooth curved surface, and having a plurality of radial flanges mutually axially spaced and defining circumferential spaces between said flanges each of such flanges, having apertures therethrough and a diameter less than said base plate, for growth of surrounding tissue thereinto.

2. Implant passageway as in claim 1, further comprising a net envelope around the portion of the socket having flanges, supported by the flanges and enclosing the grooves formed between.

3. Implant passageway as in claim 1, wherein the periphery of the flanges is substantially flush with said smooth curved surface of the end portion.

4. Implant passageway as in claim 1, further comprising rods passed axially through the apertures in the flanges.

5. Implant passageway as in claim 5, further comprising an apertured fence on said plate, spaced radially from the socket.

6. Implant passageway as in claim 5, wherein the socket and the fence project from one and the same side of the plate.

* * * * *